United States Patent
Kamijima (10) Patent No.: US 7,764,381 B2
(45) Date of Patent: Jul. 27, 2010

(54) LIGHTING DEVICE AND OPTICAL APPARATUS

(75) Inventor: Shunji Kamijima, Hara-mura (JP)

(73) Assignee: Seiko Epson Corporation, Tokyo (JP)

(*) Notice: Subject to any disclaimer, the term of this patent is extended or adjusted under 35 U.S.C. 154(b) by 355 days.

(21) Appl. No.: 11/956,624

(22) Filed: Dec. 14, 2007

(65) Prior Publication Data
US 2008/0151250 A1 Jun. 26, 2008

(30) Foreign Application Priority Data
Dec. 21, 2006 (JP) ............................. 2006-344000

(51) Int. Cl.
*G01N 21/55* (2006.01)
*G02B 7/00* (2006.01)
(52) U.S. Cl. ................... 356/445; 359/569; 359/503; 430/1
(58) Field of Classification Search ............ 356/445, 356/600–601; 340/1, 2, 3; 359/3, 12, 13, 359/15, 17, 503, 565, 558, 566, 615, 630
See application file for complete search history.

(56) References Cited

U.S. PATENT DOCUMENTS

| | | | |
|---|---|---|---|
| 4,216,344 A * | 8/1980 | Rogier ........................ 568/853 |
| 4,547,037 A * | 10/1985 | Case ............................ 359/15 |
| 4,648,892 A | 3/1987 | Kittrell et al. |
| 4,669,467 A | 6/1987 | Willett et al. |
| 4,718,417 A | 1/1988 | Kittrell et al. |
| 4,913,142 A | 4/1990 | Kittrell et al. |
| 4,967,745 A | 11/1990 | Hayes et al. |
| 5,011,255 A * | 4/1991 | Bowen et al. ................. 385/50 |
| 5,031,991 A * | 7/1991 | Nakatsu et al. ............... 385/33 |
| 5,034,010 A | 7/1991 | Kittrell et al. |
| 5,104,392 A | 4/1992 | Kittrell et al. |
| 5,106,387 A | 4/1992 | Kittrell et al. |
| 5,125,404 A | 6/1992 | Kittrell et al. |
| 5,192,278 A | 3/1993 | Hayes et al. |
| 5,199,431 A | 4/1993 | Kittrell et al. |
| 5,290,275 A | 3/1994 | Kittrell et al. |
| 5,304,173 A | 4/1994 | Kittrell et al. |
| 5,318,024 A | 6/1994 | Kittrell et al. |
| 5,370,643 A * | 12/1994 | Krivoshlykov et al. ......... 606/16 |
| 5,496,305 A | 3/1996 | Kittrell et al. |
| 5,610,734 A * | 3/1997 | Aharoni et al. ............... 359/16 |
| 5,693,043 A | 12/1997 | Kittrell et al. |
| 5,701,132 A * | 12/1997 | Kollin et al. .................... 345/8 |
| 5,712,730 A * | 1/1998 | Zarschitzky et al. ......... 359/569 |
| 5,900,955 A * | 5/1999 | Yoshikawa et al. ............ 359/17 |
| 5,980,454 A * | 11/1999 | Broome ....................... 600/176 |

(Continued)

FOREIGN PATENT DOCUMENTS

JP A-61-257638 11/1986

(Continued)

*Primary Examiner*—Sang Nguyen
(74) *Attorney, Agent, or Firm*—Oliff & Berridge, PLC (57) ABSTRACT

A lighting device includes a light source unit which emits laser beam, an optical element which receives the laser beam and releases at least a part of the entering laser beam in a direction different from the entering direction of the laser beam as illumination light, and an illumination optical path unit which is bendable and transmits the laser beam emitted from the light source unit to the optical element.

9 Claims, 6 Drawing Sheets

U.S. PATENT DOCUMENTS

| | | | |
|---|---|---|---|
| 6,069,987 A * | 5/2000 | Sasaki et al. | 385/24 |
| 6,522,403 B2 * | 2/2003 | Wilson et al. | 356/328 |
| 6,697,200 B2 * | 2/2004 | Nagaoka | 359/630 |
| 6,730,442 B1 * | 5/2004 | Sutherland et al. | 430/1 |
| 6,825,980 B2 * | 11/2004 | Dickson et al. | 359/566 |
| 7,379,219 B2 * | 5/2008 | Payne | 359/9 |
| 2002/0045811 A1 | 4/2002 | Kittrell et al. | |

FOREIGN PATENT DOCUMENTS

| | | |
|---|---|---|
| JP | A-3-295532 | 12/1991 |
| JP | A-4-17834 | 1/1992 |
| JP | A-6-123840 | 5/1994 |
| JP | A 8-224208 | 9/1996 |
| JP | A-2002-14214 | 1/2002 |

* cited by examiner

LIGHTING DEVICE AND OPTICAL APPARATUS

BACKGROUND

1. Technical Field

The present invention relates to a lighting device and an optical apparatus using a laser beam source.

2. Related Art

An endoscope device which uses a laser beam source for illumination is known. Since energy of laser beam concentrates on an extremely limited area, some technique is required for using the laser beam source as a source for emitting illumination light sufficient for uniformly illuminating a region having a certain area such as a portion of physical change caused by disease. According to a technique disclosed in JP-A-8-224208, for example, laser beam is bended by using a concave lens 11 provided at a distal end of an endoscope so as to obtain uniform illumination for a physically changed portion by disease.

Since energy of laser beam concentrates on an extremely limited area, the concave lens included in the above technique for decreasing the concentration needs to have an extremely acute angle from the center toward the peripheral area. In this case, laser beam having high energy density is applied when the center of the laser beam shifts from the center of the concave lens even slightly. As a result, light points having high luminance appear on the radiation area, and therefore uniform illumination cannot be acquired.

According to the structure of the endoscope, optical fibers are provided between the light source and the distal end portion. The endoscope distal end portion is inserted toward the physically changed area by disease by freely bending the regions of the optical fibers. In this case, it is difficult to precisely match the center of the optical element such as the concave lens disposed at the distal end of the endoscope with the center of the laser beam positioned at the other end. Thus, uniform illumination sufficient for the endoscope is difficult to obtain by using the technology disclosed in the above reference.

These problems arise not only from the case of the endoscope but also from a wide variety of cases where precise determination of relative positions of an optical element for equalizing light and a light source device is difficult under the condition of illumination constituted by light having high energy density.

SUMMARY

It is an advantage of some aspects of the invention to provide a technology for obtaining uniform illumination light by using a laser beam source to solve at least a part of the problems described above.

A lighting device according to an aspect of the invention includes a light source unit which emits laser beam, an optical element which receives the laser beam and releases at least a part of the entering laser beam in a direction different from the entering direction of the laser beam as illumination light, and an illumination optical path unit which is bendable and transmits the laser beam emitted from the light source unit to the optical element.

According to this structure, the illumination light is released in a direction different from the laser beam entering direction. Thus, laser beam passing through the optical element in the entering direction without directional change does not reach the illumination range of the illumination light. Accordingly, no spot having high luminance appears on an area to which the illumination light is applied, and therefore uniform illumination light can be obtained.

It is possible to form the optical element by a holographic optical element which releases primary diffractive light in a direction different from the entering direction of the laser beam as the illumination light. According to this structure, the range illuminated by the illumination light can have a preferable shape. The "holographic optical element" herein refers to a diffraction optical element which uses interference fringes of hologram.

It is preferable that the optical element releases the primary diffractive light such that the primary diffractive light is applied to a quadrangular region of a flat surface when the primary diffractive light is projected on the flat surface. In this case, a quadrangular area appropriate for viewing by human eyes can be illuminated by the illumination light.

It is preferable that the optical element is a computer generated hologram. According to this structure, the optical element is constructed such that the entering laser beam can be efficiently converted into the primary diffractive light as the illumination light.

It is possible to form the optical element by a diffraction grating which releases primary diffractive light in a direction different from the entering direction of the laser beam as the illumination light. In this structure, the lighting device capable of preventing appearance of a high luminance spot on the area to which the illumination light is applied can be similarly provided.

It is preferable that the lighting device further includes an absorbing unit disposed on the side opposite to the laser beam entering side with respect to the optical element in the laser beam entering direction extended from the optical element to absorb light and prevent emission of the light to the outside of the lighting device.

According to this structure, emission of laser beam having passed through the optical element in the entering direction without directional change to the outside of the lighting device can be prevented. Thus, the possibility that laser beam is applied to an object not intended by the user can be lowered.

An optical apparatus including the lighting device having any one of the above structures can be constructed as follows. This optical apparatus includes an image processing unit which receives light reflected by an object and forms an image of the object, and a reflection optical path unit which is bendable and so constructed as to transmit reflection light reflected by the object having received the illumination light to the image processing unit.

In this case, the image of the object illuminated by the illumination light of the lighting device can be produced by the image processing unit.

It is preferable that the optical element and the reflection optical unit are constructed such that the range of the object reflecting the reflection light to be received by the reflection optical path unit does not include an area of the object which can be illuminated by light emitted in the laser beam entering direction extended from the optical element.

In this case, a high luminance spot produced by laser beam having passed through the optical element in the entering direction without directional change does not appear on the range of the object reflecting the reflection light to be received by the reflection optical path unit. Thus, an image can be obtained under uniform illumination.

It is preferable that the light source unit includes a first light source which emits red laser beam, a second light source which emits green laser beam, and a third light source which emits blue laser beam. In addition, it is preferable that the optical element is so constructed as to emit at least a part of the red laser beam, a part of the green laser beam, and a part of the blue laser beam to a mutually overlapping range on the object as illumination lights. According to this structure, a color image can be produced by the image processing unit.

It is preferable that the illumination optical path unit includes a first illumination optical path which is bendable and transmits the red laser beam emitted from the first light source to the optical element, a second illumination optical path which is bendable and transmits the green laser beam emitted from the second light source, and a third illumination optical path which is bendable and transmits the blue laser beam emitted from the third light source. In addition, it is preferable that the optical apparatus further includes a holding unit which holds the first through third illumination optical path and the reflection optical path unit in two lines and two rows.

According to this structure, the first through third illumination optical path and the reflection optical path unit are collectively held, and the relative positions of the three illumination optical path and the reflection optical path unit are not easily changed when these optical units are bended. Thus, a preferable image can be obtained even when the illumination optical path units and the reflection optical path unit are bended.

The invention has broad applicability. For example, the invention is applicable to lighting unit, optical apparatus, image acquisition apparatus, lighting method, image acquisition method, computer program for providing functions included in these methods or apparatuses, recording medium storing this computer program, data signals containing this computer program and provided in carrier waves, and others.

BRIEF DESCRIPTION OF THE DRAWINGS

The invention will be described with reference to the accompanying drawings, wherein like numbers refer to like elements.

DESCRIPTION OF EXEMPLARY EMBODIMENTS

A. First Embodiment

Figure 1:
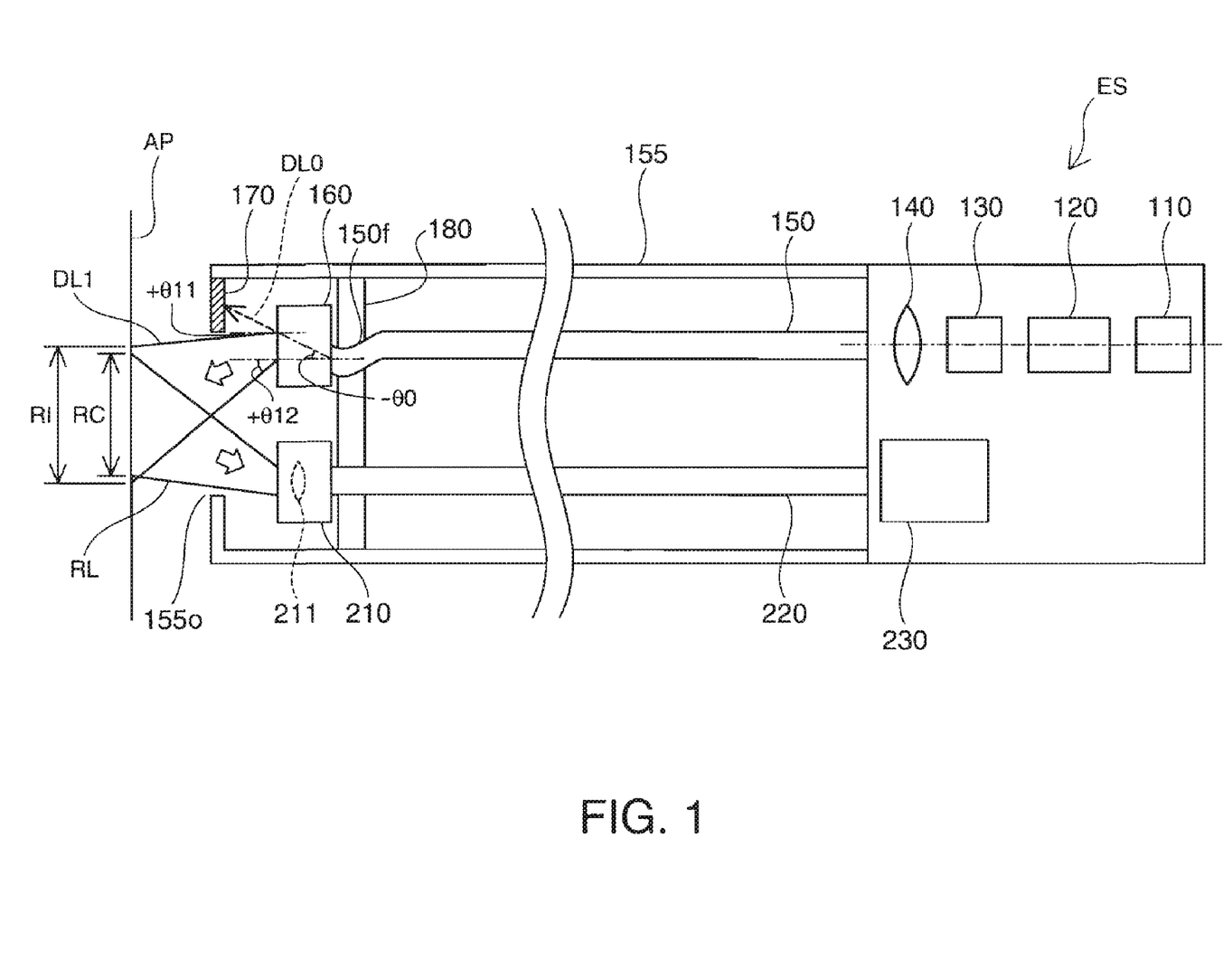
FIG. 1 is a cross-sectional view of an endoscope ES according to a first embodiment of the invention.

FIG. 1 is a cross-sectional view of an endoscope ES according to a first embodiment of the invention. The endoscope ES includes a laser diode 110, a second higher harmonic wave generator 120, a resonator 130, a lens 140, optical fibers, a computer generated hologram 160, an absorber 170, and a holder 180. The illumination optical path unit is the optical filters 150. The endoscope ES further includes a light receiving unit 210, optical fibers 220, and a camera 230.

The optical fibers 150, the computer generated hologram 160, the light receiving unit 210, and the optical fibers 220 of the endoscope ES are covered by a bendable cover 155 and the absorber 170. The cover 155 has an opening 155o. A part of light emitted from the computer generated hologram 160 (hereinafter abbreviated as "CGH 160") passes through the opening 155o to be applied to an affected part AP. Reflection light RL reflected by the affected part AP passes through the opening 155o to be received by the light receiving unit 210.

The laser diode 110 emits laser beam. The second higher harmonic wave generator 120 receives the laser beam from the laser diode 110 and generates laser beam having a frequency twice higher than the frequency of the received laser beam. The resonator 130 resonates the laser beam received from the second higher harmonic wave generator 120. Then, the laser beam released from the resonator 130 enters the optical fibers 150 via the lens 140.

The optical fibers 150 transmit laser beam to the CGH 160. A distal end portion 150f of the optical fibers 150 is bended and connected to the CGH 160. Thus, the optical fibers 150 receive the laser beam at a predetermined angle of $-\Theta 0$ with respect to a center line CI of the CGH 160. In this specification, an angle of a direction on the light receiving unit 210 side with respect to the center line CI of the CGH 160 is a positive angle, and an angle of a direction on the opposite side with respect to the center line CI is a negative angle.

Figure 2:
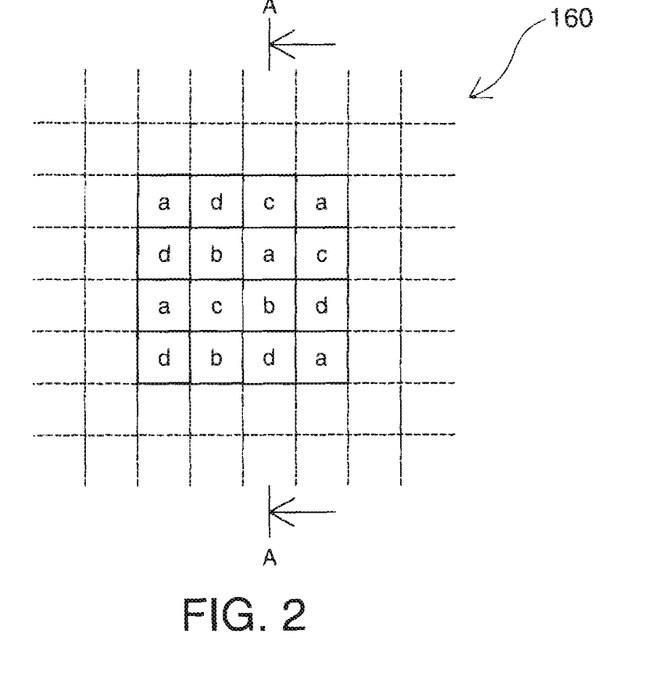
FIG. 2 is a front view showing an enlarged part of a CGH (computer generated hologram) 160.
Figure 3:
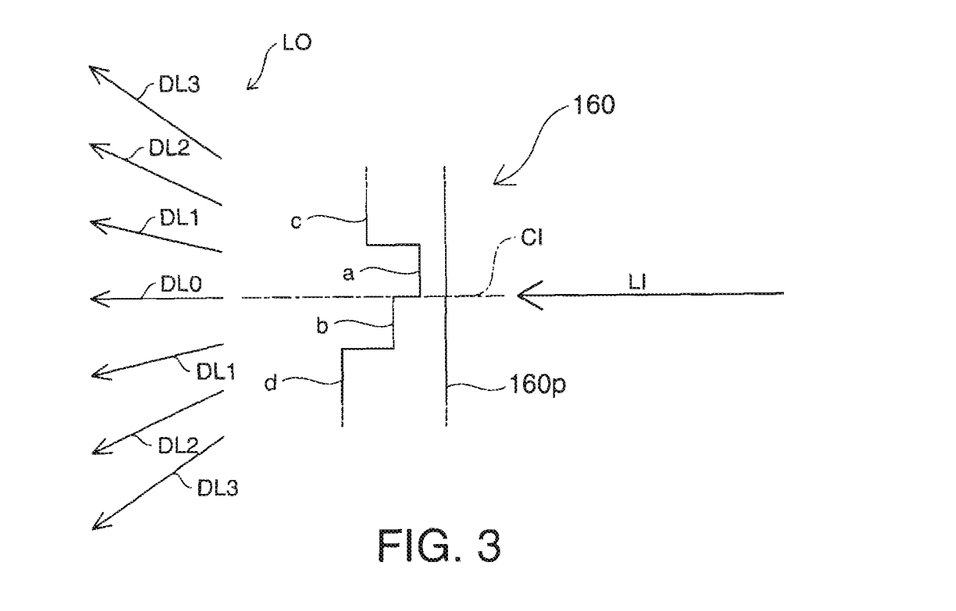
FIG. 3 is a cross-sectional view of the CGH 160 taken along a line A-A in FIG. 2.

FIG. 2 is a front view showing an enlarged part of the CHG 160. FIG. 3 is a cross-sectional view taken along a line A-A in FIG. 2. The CGH 160 is substantially plate-shaped, and has a flat surface 160p on one side and a concaved and convexed surface on the other side. A line perpendicular to the surface 160p is referred to as the center line CI of the CGH 160. The CGH 160 has a plurality of rectangular areas a through d extending along the center line CI and having different thicknesses. The thicknesses of the rectangular areas a through d increase in the order of a to d. A number of the rectangular areas a through d having different thicknesses are provided on the CGH 160.

The CGH 160 having this structure emits transmitted light DL0, primary diffracted light DL1, secondary diffracted light DL2, tertiary diffracted light DL3, and other lights produced from entering light LI in angle ranges different from one another. FIG. 3 showing the transmitted light DL0, the primary diffracted light DL1, the secondary diffracted light DL2, and the tertiary diffracted light DL3 for explanation does not accurately indicate the respective directions of the lights emitted from the CGH 160 in this embodiment. In this specification, lights emitted from the CGH 160 including the transmitted light DL0, the primary diffracted light DL1, the secondary diffracted light DL2, and the tertiary DL3 are collectively referred to as emitted lights LO in some cases.

The CGH 160 is designed by a predetermined simulation method such as iterative Fourier method. The CGH 160 in this embodiment releases most of the energy of the entering light LI as the primary diffractive light DL1. The CGH 160 thus emits little amount of the transmitted light DL0 (also referred to as "zero degree diffractive light" in this specification) and the secondary or higher degree diffractive lights DLi (i=2, 3 or larger).

The CGH 160 in this embodiment radially emits the primary diffractive light DL1 such that the cross section of the diffractive light DL1 crossing the traveling direction of the diffractive light DL1 has a quadrangular shape. The primary diffractive light DL1 shown in FIG. 3 is indicated by an arrow for easy understanding, but practically the primary diffractive light DL1 is radiated at angles within a predetermined range.

In the structure shown in FIG. 1, the entering light enters the CGH 160 at the predetermined angle of $-\Theta 0$. Thus, when the transmitted light DL0 is released from the CGH 160, if any, the angle of the transmitted light DL0 with respect to the center line CI of the CGH 160 is −Θ0 without change.

The absorber 170 is disposed on the side opposite to the side where the laser beam enters the CGH 160 in the entering direction of the laser beam extended from the CGH 160 (direction of transmitted light DL0 in FIG. 1). The absorber 170 is formed by a black aluminum plate. When the transmitted light DL0 is released from the CGH 160, if any, the absorber 170 absorbs the transmitted light DL0 and prevents emission of the light DL0 to the outside of the endoscope ES.

The primary diffractive light DL1 is released at angles from +Θ11 to +Θ12 from the CGH 160. Then, the primary diffractive light DL1 passes through the opening 155o to be applied to a radiation area RI of the affected portion AP.

The affected portion AP receives the primary diffractive light DL1 as illumination light emitted from the CGH 160, and reflects the illumination light as reflection light. The light receiving unit 210 receives at least a part RL of the reflection light reflected by an image acquisition portion RC contained in the radiation area RI of the affected portion AP. The light receiving unit 210 has an eccentric lens 211. The light receiving unit 210 receives the reflection light RL reflected by the image acquisition portion RC located at a position shifted from the front of the light receiving unit 210 by using the eccentric lens 211. Then, the reflection light RL is collimated by the eccentric lens 211 and supplied to the optical fibers 220.

The optical fibers 220 supply the collimated light received from the eccentric lens 211 to the camera 230. The camera 230 shoots a picture using the light received from the optical fibers 220.

The positions around the ends of the optical fibers 150 and 220 on the affected portion AP side are held by the holder 180. The optical fibers 150 and 220 in the area from the holder 180 toward the affected portion AP covered by the cover 155 are scarcely bendable. Thus, when the optical fibers 150 and 220 covered by the cover 155 are bended in this embodiment, the relative positions and postures of the optical fibers 150 and the optical fibers 220 do not easily change. As a result, the direction of the illumination light DL1 is not easily varied, and therefore a high-quality picture image of the affected portion can be obtained.

Figure 4:
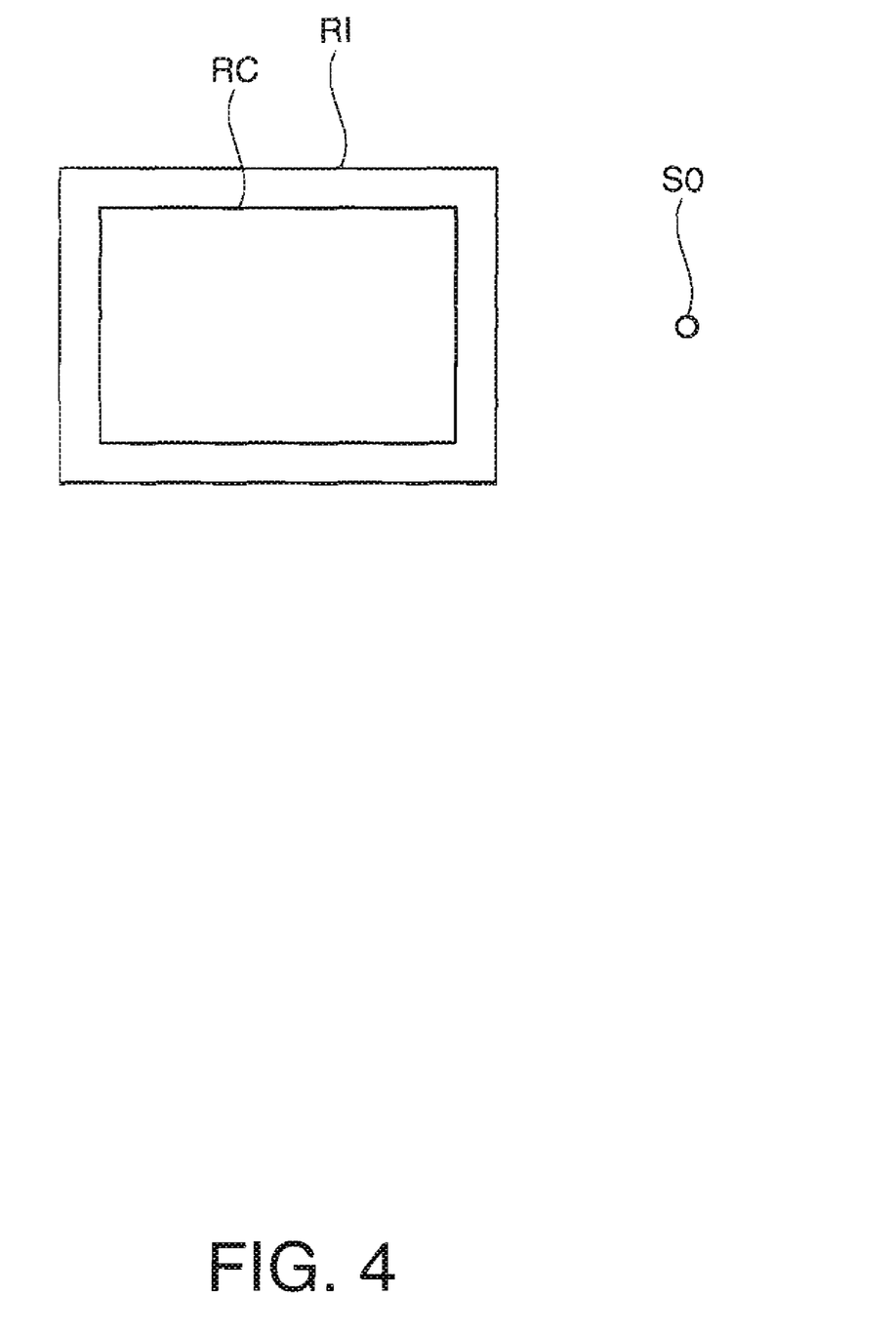
FIG. 4 shows the relationship between a radiation area RI and an image acquisition portion RC.

FIG. 4 shows the relationship between the radiation area RI as a range of the affected portion to which the primary diffractive light DL1 released from the CGH 160 is applied, and the image acquisition portion RC reflecting the reflection light to be received by the light receiving unit 210. When the affected portion AP is a flat surface in parallel with a reference surface 160p of the CGH 160, the area RI to which the primary diffractive light DL1 is applied has a rectangular shape. When the affected portion AP is a flat surface in parallel with the reference surface 160p of the CGH 160, the image acquisition portion RC reflecting the reflection light to be received by the light receiving unit 210 becomes a rectangular range contained in the area RI. When, the affected portion AP is a flat surface which is not parallel with the reference surface 160p of the CGH 160, the area RI has a quadrangular shape.

When the transmitted light DL0 is released from the CGH 160 under the condition where the absorber 170 (see FIG. 1) is not equipped, a high luminance spot S0 produced by the transmitted light DL0 appears on the affected portion AP. The CGH 160 and the light receiving unit 210 of the endoscope ES according to this embodiment are designed such that the transmitted light DL0 and the illumination light DL1 are released in difference directions (see FIG. 1), and that the spot S0 does not overlap with the area RI and the image acquisition portion RC. Thus, the high luminance spot S0 does not exist within the image acquisition portion RC of the affected portion to be shot by the camera 230 under illumination by the illumination light. Accordingly, a picture of the affected portion can be obtained under the environment of preferable illumination.

B. Second Embodiment

Figure 5:
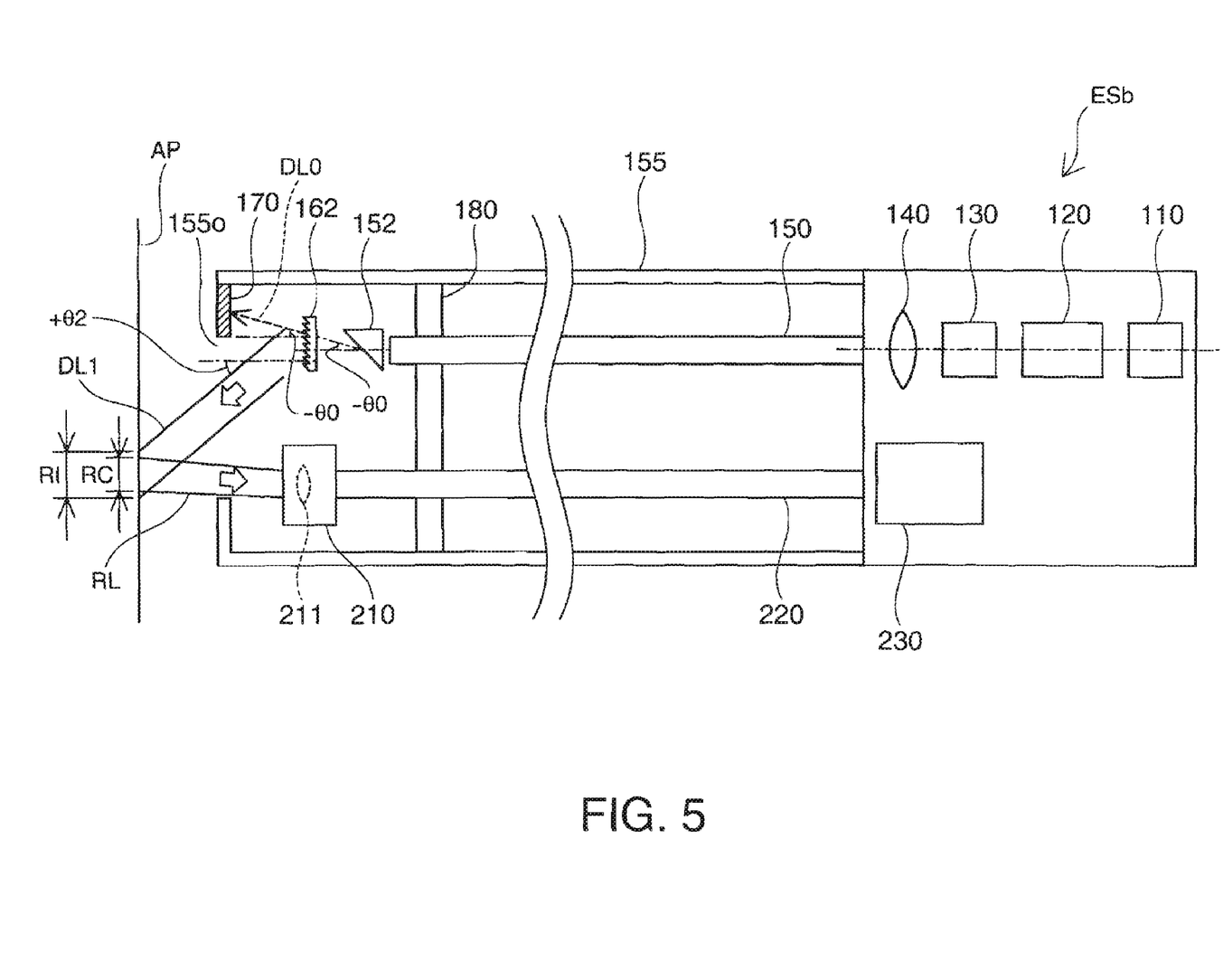
FIG. 5 is a cross-sectional view of an endoscope ESb according to a second embodiment of the invention.

FIG. 5 is a cross-sectional view showing an endoscope ESb according to a second embodiment of the invention. The endoscope ESb in the second embodiment has a prism 152 in lieu of the bended distal end portion 150f of the optical fibers 150. The prism 152 and optical fibers 150 are the illumination optical path unit. The endoscope Esb in the second embodiment has a diffraction grating 162 in lieu of the CGH 160. Other parts of the endoscope ESb in the second embodiment are similar to those of the endoscope ES in the first embodiment.

The prism 152 changes the direction of laser beam received from the optical fibers 150 and supplies the resultant laser beam to the diffraction grating 162. The entering direction of the laser beam with respect to the center line of the diffraction grating 162 is indicated by an angle −Θ0.

The diffraction grating 162 is an optical element having repetitive patterns along one direction (up-down direction in FIG. 5). In FIG. 5, the characteristics of the repetitive patterns are emphasized. The diffractive grating 162 receives entering light at the angle of −Θ0 with respect to the center line, and releases the primary diffractive light DL1 at an angle of +Θ2 with respect to the center line as an angle different from the angle −Θ0. The transmitted light DL0 passing through the diffraction grating 162 is released at the angle of −Θ0 with respect to the center line, and absorbed by the absorber 170.

According to this embodiment, the radiation area RI of the affected portion AP can be illuminated by using the primary diffractive light DL1 produced by the diffraction grating 162 as illumination light similarly to the first embodiment. In this case, the high-luminance spot S0 does not appear within the image acquisition portion RC to be shot by the camera 230 under illumination by the illumination light.

C. Third Embodiment

Figure 7:
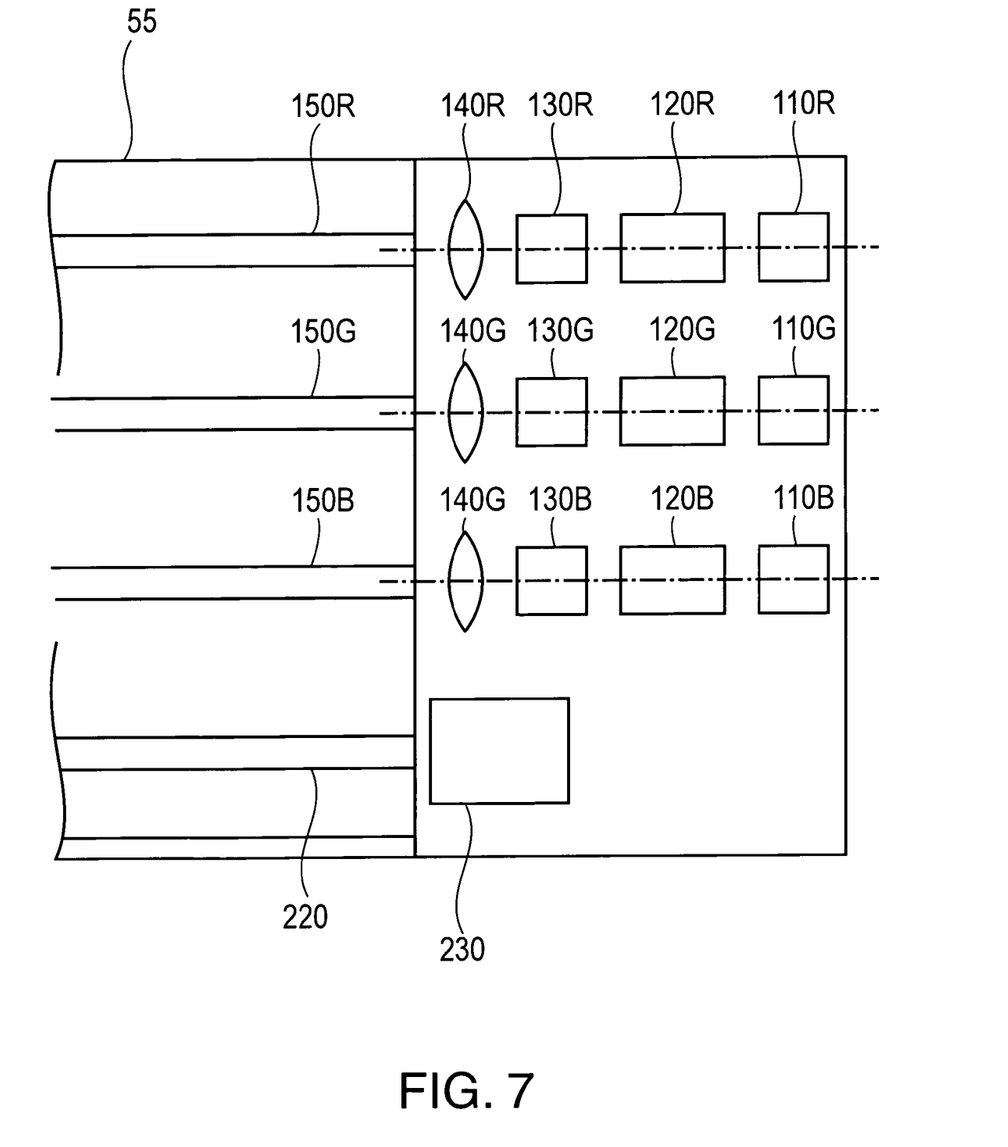
FIG. 7 is a cross-sectional view of an endoscope according to a third embodiment.

The endoscope ES according to the first embodiment has a set of the laser diode 110, the second higher harmonic wave generator 120, the resonator 130, the lens 140, the optical fibers 150, the CGH 160, and the absorber 170. Laser diodes 110r, 110g and 110d, second higher harmonic wave generators 120r, 120g and 120b, resonators 130r, 130g and 130d, and lens 140r, 140g and 140b are the first, second and third light sources respectively, as shown in FIG. 7. An endoscope ESc in a third embodiment has three sets of these components, and emits red light, green light and blue light from CGHs 160r, 160g and 160b each of which is included in the corresponding set. The red light, green light and blue light are applied to the overlapping area RI of the affected portion AP positioned at a predetermined distance from the CGHs 160r, 160g and 160b. Other points of the endoscope ESc in the third embodiment are similar to those of the endoscope ES in the first embodiment.

Figure 6:
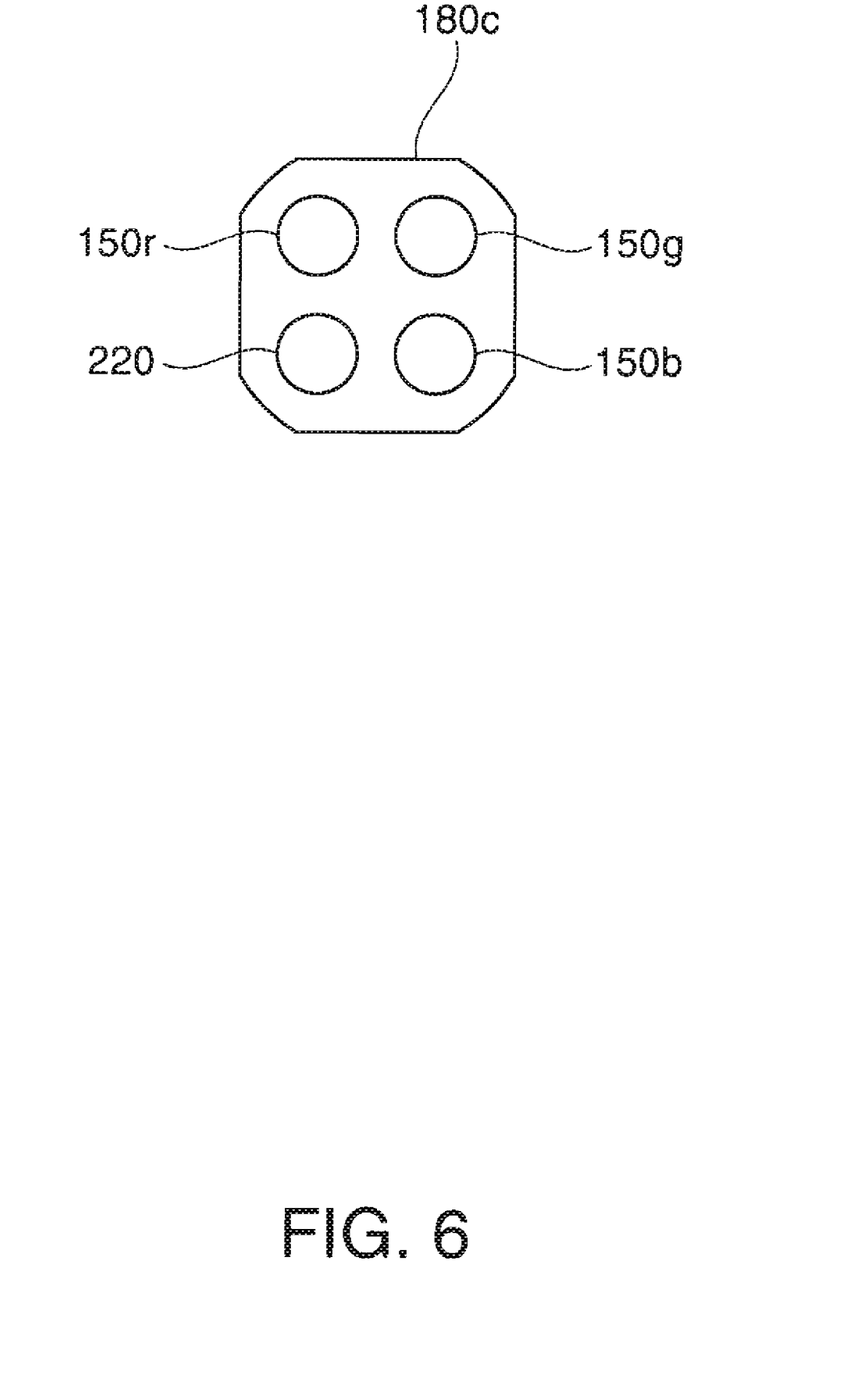
FIG. 6 is a plan view of a holder 180c.

FIG. 6 is a plan view showing a holder 180c which holds three optical fibers 150r, 150g and 150b for transmitting laser beam and the optical fibers 220 for transmitting reflection light reflected by the affected portion AP. The endoscope ESc in the third embodiment has laser diodes 110r, 110g and 110b for emitting laser beams having different frequencies.

According to the signs denoting the respective components of the endoscope Esc, a component denoted by the sign "r" is an element contained in the illumination optical system for red light. Similarly, a component denoted by the sign "g" is an element contained in the illumination optical system for green light, and a component denoted by the sign "b" is an element contained in the illumination optical system for blue light.

The laser beams in respective colors pass through an illumination optical path including first, second and third illumination optical paths corresponding to second higher harmonic wave generators 120r, 120g and 120b, resonators 130r, 130g and 130b, lenses 140r, 140g and 140b, and the optical fibers 150r, 150g and 150b, before being released from the CGHs 160r, 160g and 160b and applied to the area RI as illumination lights in red, green and blue. Due to this, the light receiving unit 210 can receive color reflection lights from the image acquisition portion RC. Thus, the camera 230 can obtain a color image in the third embodiment.

The optical fibers 150r are optical fibers for transmitting red laser beam. The optical fibers 150g are optical fibers for transmitting green laser beam. The optical fibers 150b are optical fibers for transmitting blue laser beam.

The holder 180c shown in FIG. 6 holds the optical fibers 150r, 150g, 150b and 220 in two lines and two rows in the vicinity of the ends of the optical fibers 150r, 150g, 150b and 220 on the affected portion AP side. The attachment position of the holder 180c is the same as the position of the holder 180 in the endoscope ES in the first embodiment shown in FIG. 1.

The optical fibers 150r, 150g, 150b and 220 in the area from the holder 180c toward the affected portion AP covered by the cover 155 are scarcely bendable. Thus, when the optical fibers 150r, 150g, 150b and 220 covered by the cover 155 are bended in the third embodiment, the relative positions of the optical fibers 150r, 150g, 150b and 220 do not easily change. As a result, the directions of the illumination lights in red, green and blue are not easily varied, and therefore a high-quality picture image of the affected portion can be obtained.

D. Modified Examples

This invention is not limited to the examples and embodiments described herein, but may be practiced otherwise without departing from the scope of the invention. For example, the following modifications may be made.

D1. Modified Example 1

The endoscope Esc in the third embodiment is so constructed as to emit red laser beam, green laser beam and blue laser beam. However, the lights to be applied to the target object may have colors other than red, green and blue. For example, red, green and blue lights may be synthesized before those lights are supplied to the optical fibers 150, and white light obtained after synthesis may be supplied to the optical fibers 150 as illumination light. In this example, the target object is illuminated by white light, and therefore a color image of the target object can be obtained by the image processing unit such as the camera 230.

The light to be applied to the target object may be infrared light or ultraviolet light. When the laser diode 110, the second higher harmonic wave generator 120, the resonator 130, the lens 140, and other components are so designed as to emit such non-visible light, it is preferable that the camera 230 as the image processing unit and the like are so structured as to form an image of the target object by receiving reflection light constituted by non-visible illumination light.

D2. Modified Example 2

The structure in the third embodiment contains the CGHs 160r, 160g and 160b for red light, green light and blue light. These optical elements may be either provided separately or formed integrally with one another. In the structure containing the optical elements for different color lights formed integrally with one another, the emission directions of the respective color lights are not easily shifted from one another when the areas of the optical fibers are bended. Thus, a preferable image can be obtained even when the areas of the optical fibers are bended.

D3. Modified Example 3

In these embodiments, optical fibers freely bendable at arbitrary positions are used as bendable optical path unit. It is possible, however, to form the optical path unit by a structure as a combination of prism, lens, mirror and other parts capable of varying the angle of the light direction to an arbitrary angle at a predetermined position. That is, the optical path unit for illumination light may have any structure as long as it is bendable and can transmit light emitted from the light source to the optical element such as CGH. Also, the optical path unit for reflection light may have any structure as long as it is bendable and can transmit reflection light reflected by the target object.

D4. Modified Example 4

According to the first embodiment, the distal end 150f of the optical fibers 150 is bended at the holder 180 (see FIG. 1). However, the optical fibers 150 may be bended at a portion having a length ten times larger than the outside diameter of the optical fibers or larger, for example, by using a holder which holds plural positions of the optical fibers 150 along its longitudinal direction. In this case, the curvature of the optical fibers is small, and therefore the possibility of breakage of the optical fibers can be lowered. In this structure, the optical fibers 150 gently bended for transmitting illumination light and the optical fibers 220 for transmitting reflection light may cross each other.

D5. Modified Example 5

According to the first and second embodiments, the primary diffractive light is used as illumination light. However, the secondary diffractive light or higher degree light produced from an optical element may be used as illumination light.

In these embodiments, the CGH 160 and the diffraction grating 162 are used as the optical elements for releasing at least a part of entering laser beam in a direction different from the entering direction of the laser beam. However, other structure may be employed as an optical element offering this function. For example, a diffusion plate having light diffusing and transmitting characteristics such as ground glass may be used in lieu of the CGH 160 or the diffraction grating 162. In this case, light diffused in a direction different from the entering direction of laser beam is used as illumination light.

D6. Modified Example 6

In the first embodiment, a computer generated hologram 160 is used as the optical element for emitting at least a part of entering laser beam in a direction different from the entering direction of the laser beam. However, a holographic optical element of a type different from the computer generated hologram may be employed. For example, using a rectangular white plate with black background, a holographic optical element for recording white rectangular hologram of the plate by using light beam having mutually coherent components may be used in lieu of the CGH 160.

D7. Modified Example 7

In these embodiments, the absorber 170 for absorbing transmitted light is made of aluminum. However, the absorber 170 may be constituted by other materials such as ABS (acrylonitrile butadiene styrene).

D8. Modified Example 8

In these embodiments, the camera is used as the image processing unit for forming an image of the target object. However, other structures such as a recording device for recording an image on a recording medium (e.g., digital camera, Polaroid camera, and printer), and a display unit for displaying an image on a display (e.g., optical system screen, liquid crystal monitor, and projector) may be used.

D9. Modified Example 9

In these embodiments, the endoscope for obtaining an image of the affected portion has been discussed as an example of the invention. However, the invention is applicable to other devices such as a device for obtaining an internal picture image within a structure or at a scene of accident. Alternatively, the invention is applicable to a lighting device (illumination device) which does not include a structure for processing reflection light.

The entire disclosure of Japanese Patent Application No. 2006-344000, filed Dec. 21, 2006 is expressly incorporated by reference herein.

What is claimed is:

1. An optical apparatus for use with an object comprising:
    a light source unit which emits a laser beam;
    an optical element which receives the laser beam and releases at least a part of the entering laser beam in a direction different from the entering direction of the laser beam as illumination light, the optical element being a holographic optical element which releases primary diffractive light in a direction different from the entering direction of the laser beam as the illumination light; and
    an illumination optical path unit which is bendable and transmits the laser beam emitted from the light source unit to the optical element;
    an image processing unit which receives light reflected by the object and forms an image of the object; and
    a reflection optical path unit which is bendable and constructed to transmit reflection light reflected by the object after receiving the illumination light to the image processing unit; and
    wherein the optical element and the reflection optical path unit are constructed such that the range of the object reflecting the reflection light to be received by the reflection optical path unit does not include an area of the object which can be illuminated by light emitted in the laser beam entering direction extended from the optical element.

2. The optical apparatus according to claim 1, wherein the optical element releases the primary diffractive light such that the primary diffractive light is applied to a quadrangular region of a flat surface when the primary diffractive light is projected on the flat surface.

3. The optical apparatus according to claim 2, wherein the optical element is a computer generated hologram.

4. The optical apparatus according to claim 1, wherein the optical element is a diffraction grating which releases primary diffractive light in a direction different from the entering direction of the laser beam as the illumination light.

5. The optical apparatus according to claim 1, further comprising an absorbing unit disposed on the side opposite to the laser beam entering side with respect to the optical element in the laser beam entering direction extended from the optical element to absorb light and prevent emission of the light to the outside of the lighting device.

6. The optical apparatus according to claim 1, wherein:
    the light source unit includes
    a first light source which emits red laser beam,
    a second light source which emits green laser beam, and
    a third light source which emits blue laser beam; and
    the optical element is so constructed as to emit at least a part of the red laser beam, a part of the green laser beam, and a part of the blue laser beam to a mutually overlapping range on the object as illumination lights.

7. The optical apparatus according to claim 6, wherein:
    the illumination optical path unit includes
    a first illumination optical path which is bendable and transmits the red laser beam emitted from the first light source to the optical element,
    a second illumination optical path which is bendable and transmits the green laser beam emitted from the second light source to the optical element, and
    a third illumination optical path which is bendable and transmits the blue laser beam emitted from the third light source to the optical element; and
    the optical apparatus further includes a holding unit which holds the first through third illumination optical units and the reflection optical unit in two lines and two rows.

8. The optical apparatus according to claim 1, wherein the illumination optical path unit includes optical fibers.

9. The optical apparatus according to claim 8, wherein the optical element is disposed within a bendable cover.

* * * * *